United States Patent [19]

McKeating

[11] Patent Number: 5,078,721

[45] Date of Patent: Jan. 7, 1992

[54] DEVICE FOR SURGICAL LIGATION

[76] Inventor: John A. McKeating, 1074 Osage Dr., Pittsburgh, Pa. 15235

[21] Appl. No.: 367,348

[22] Filed: Jun. 16, 1989

[51] Int. Cl.$^5$ .............................................. A61B 17/04
[52] U.S. Cl. ................................... 606/139; 606/148; 606/232; 606/228
[58] Field of Search ............................. 606/138-146, 606/148-151, 228-233

[56] References Cited

U.S. PATENT DOCUMENTS

| | | | |
|---|---|---|---|
| 3,802,438 | 4/1974 | Wolvek | 606/232 |
| 4,038,988 | 8/1977 | Perisse | 606/139 |
| 4,128,100 | 12/1978 | Wendorff | 606/141 |
| 4,423,729 | 1/1984 | Gray | 606/138 X |
| 4,553,543 | 11/1985 | Amarasinghe | 606/148 |
| 4,796,626 | 1/1989 | DeVries | 606/148 |
| 4,898,156 | 2/1990 | Gattuma et al. | 606/232 X |
| 4,899,743 | 2/1990 | Nicholson et al. | 606/139 |
| 4,901,721 | 2/1990 | Hakki | 606/232 X |
| 4,911,164 | 3/1990 | Roth | 606/148 |

Primary Examiner—Robert A. Hafer
Assistant Examiner—Kerry Owens

[57] ABSTRACT

A ligature is described in which one end of the ligature is made firm and inserted into a sleeve to facilitate passage under a tubular vessel and retrieval of both ends.

1 Claim, 5 Drawing Sheets

FIG. 2A
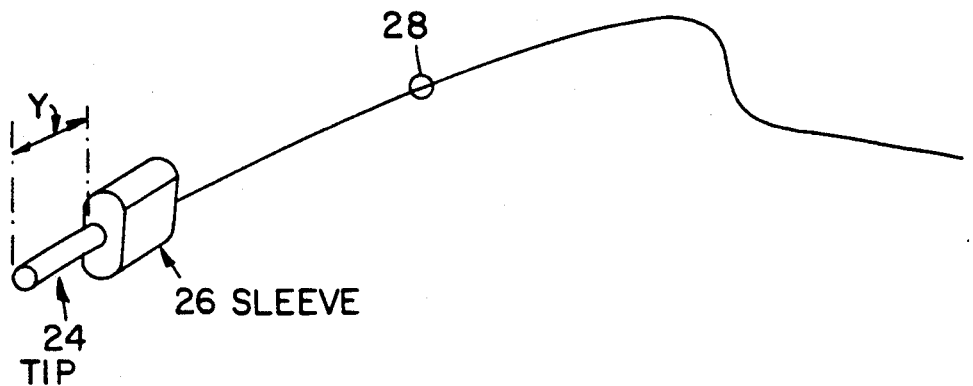
FIG. 2B
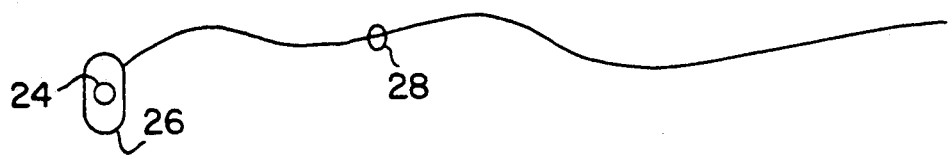
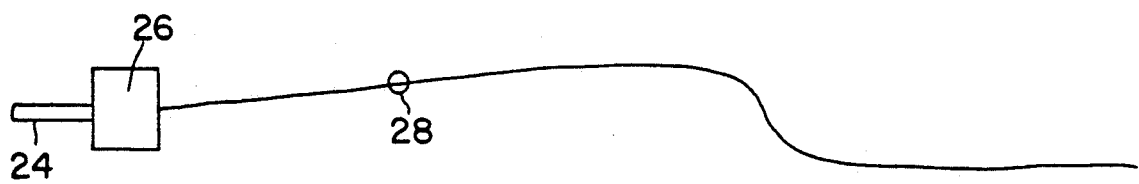
FIG. 2C
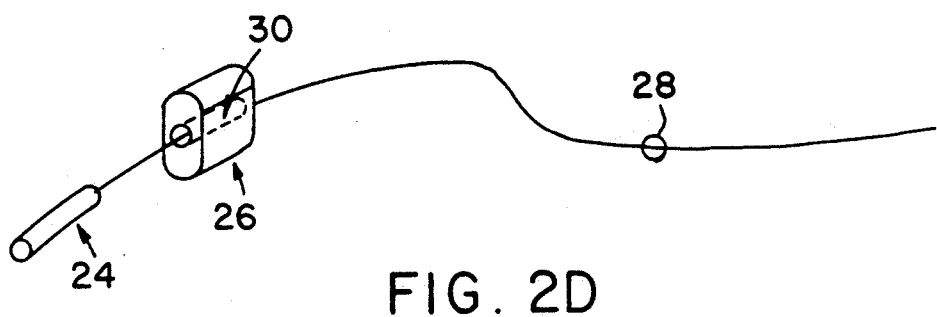
FIG. 2D

DEVICE FOR SURGICAL LIGATION

BACKGROUND OF THE INVENTION

In the course of a surgical procedure blood vessels and other structures must often be ligated, or tied-off, and divided between two such ligatures. Dividing the vessel between two ligatures prevents the cut ends of the vessel from bleeding. These ligatures are simply lengths of silk thread or other suture material. When this procedure takes place in small confines or deep areas inaccessible to the operator's hands various instruments or "clamps" are used to pass the ligatures under the vessel.

In the current method Operator A, the primary surgeon, dissects or separates the surrounding tissues away from the vessel to create enough space for a right-angle clamp to be placed under the vessel. The tips or jaws of this right angle clamp extend beyond the vessel and are kept in an open position to await passage of the ligature from Operator B, the assisting surgeon. Operator B is handed a clamp whose jaws hold one end of the ligature to be passed. The other end of the ligature is free. Operator B grasps his clamp in hand 1. To facilitate passage to Operator A's clamp, tension must be applied to the free end of the ligature. This imparts stability and linearity to the ligature so that it may be efficiently maneuvered into the jaws of Operator A's clamp. This requires that Operator B employ hand 2 which had previously been retracting other organs to provide exposure, suctioning blood from the operative field, or performing other vital functions. Tension may be applied to the free end of the ligature by a third Operator but this is cumbersome because he or she is often removed from the operative field with a poor view. If no tension is applied to the free end of the limp ligature passage is uncertain and cumbersome and Operator A must search for the free end of the ligature to complete the ligation.

Another disadvantage of the current system is that the jaws of Operator B's clamp must be placed beneath Operator A's clamp so that the ligature may be passed. This can be difficult because of space constraints and frequently requires additional dissection. Structures underlying the vessel to be divided may be injured by Operator B's clamp.

I described, by way of example, two changes in the design of the ligature which eliminate the problems detailed above.

SUMMARY OF THE PRESENT INVENTION

The tip of the ligature to be placed under the vessel first is specially prepared and thus made suitably firm. This may be accomplished by the application of biologically inert material such as metal, absorbable plastic, molten or pressed material to the end of the ligature. This may also be achieved by altering the composition or construction of the suture material itself, for example, by weaving silk into a thicker firm end or by interspersing wire into the tip of the ligature. The edges of the tip are smooth and rounded to prevent injury to the vessel. In cross section the tip may be circular, square, hexagonal, octagonal or any suitable polygonal shape to accommodate the surfaces of Operator A's clamp. The tip is to be prepared and produced in a range of lengths and diameters appropriate for the size of ligature and to apply to a variety of operative situations. The firm tip enables Operator B to accurately place the ligature within the jaws of Operator A's clamp and obviates the need for tension to be placed on the free end of the ligature. This maneuver is performed totally by hand 1, thereby allowing hand 2 to continue to perform other vital functions.

A sleeve may be constructed from the same material as the tip or from different material. There is a channel through the center of the sleeve resembling an opening or hole in a doughnut. The firm tip of the ligature is placed within the sleeve and protrudes for a distance so that it may be easily grasped by the jaws of Operator A's clamp. The tip may be held into the sleeve by a weak adhesive or a thin strand of its own material. The end of the tip which fits into the sleeve may be shaped in a conical fashion so that it is held into the sleeve by friction. By whatever method the tip is held into the sleeve, when pulled gently the tip should dislodge from the sleeve and the ligature will then trail through the channel in the sleeve with minimum drag or friction. The sleeve remains within the jaws of Operator B's clamp and is then held up out of the wound so that the trailing end of the ligature is presented to Operator A who then completes the ligation.

The shape of the sleeve is important since it must accommodate the surfaces of the jaws of Operator B's clamp. In cross-section it may be round, square, hexagonal, octagonal or any suitable polygonal shape. The sleeve may be rotated in the long axis of Operator B's clamp so that Operator A's clamp may be approached from a variety of directions.

Alternatives to the sleeve described above advantageously include a sleeve permanently affixed to a handle so that multiple ligatures are passed in succession by one sleeve and handle. In conjunction with a packaging technique wherein the ligature tips project up from the surface of a container, this instrument can be rapidly reloaded. The handle/sleeve is placed down over the tip which is secured into place within the sleeve and withdrawn from the package with the ligature trailing the tip out of the package. Numerous ligatures are placed within one such package.

Another embodiment involves the use of a long thin tubular vessel resembling a thin drinking straw. Multiple ligatures are stored within the hollow center of the tube. The firm tip of the first ligature projects out of the end of the tube for a distance so that it can be easily grasped by the jaws of Operator A's clamp. The "free" end is attached to the firm tip of the second ligature in the tube so that the second tip is pulled into position when the first ligature is extracted. A small amount of force separates the "free" end of the first ligature from the firm tip of the second. A slightly greater amount of force is necessary to dislodge the firm tip of the second ligature from the orifice of the hollow tube. Another alternative is to have the coiled ligatures spring loaded within the hollow handle so that when one ligature is withdrawn the tip of the next ligature protrudes from the tip of the handle. Multiple ligatures are contained within one such tube with the last tip color coded to signify that the dispenser is nearly empty. Once again, a sleeve is not necessary because the free end of the first ligature is tethered loosely to the firm tip of the second and is presented to Operator A up out of the wound. There are other methods of packaging multiple ligatures within a tubular dispenser but this does not alter the concept of a one handed passage of the ligature.

In another embodiment a hole is placed into the end of Operator B's clamp in the frontal plane perpendicular to the long axis of the clamp. The prepared and firm ligature tip is placed directly into the jaw of the clamp without a sleeve. The free end of the ligature is threaded through the channel in the clamp and this channel serves the same functions as the sleeve. This small channel does not interfere with the other functions of the clamp.

The first system described is preferred because it allows for rotation of the sleeve in the long axis of the clamp which affords the advantage of being able to approach Operator A's clamp from above, below or straight on. This system also utilizes familiar instruments and therefore minimizes cost and the necessity of learning to handle new instruments.

All of the above devices would be sterilized along with the suture material by conventional methods. The preferred materials for the construction of the tip and sleeve would be inert or absorbable.

BRIEF DESCRIPTION OF THE DRAWINGS

The invention will now be described, by way of example, with reference to the accompanying drawings in which:

FIGS. 2a, b, c, d are oblique, front and side views of the new device, and the tip shown dislodged from the sleeve;

DETAILED DESCRIPTION OF THE DRAWINGS

Figure 1:
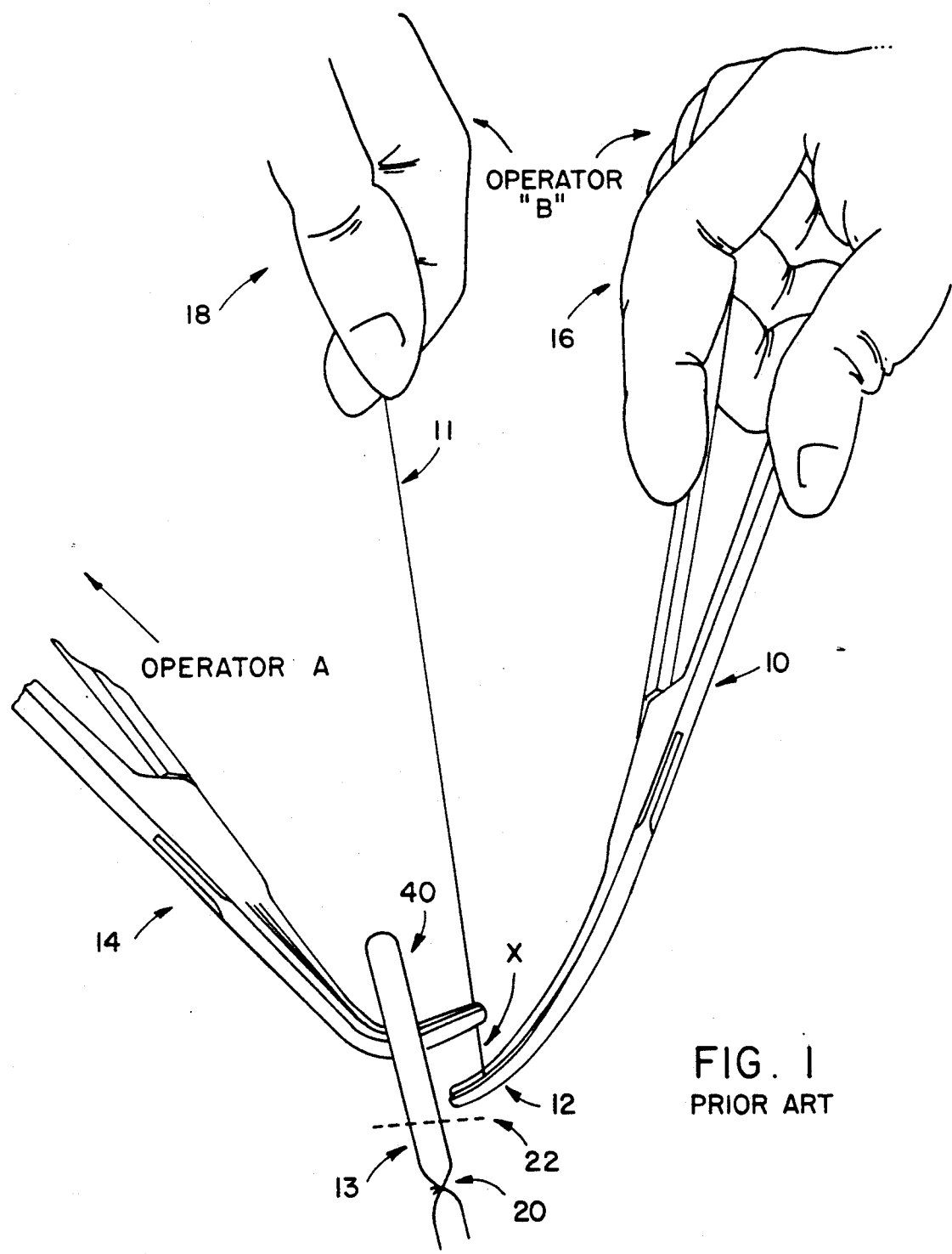
FIG. 1 is an oblique view of a ligature being passed by the present known method.

FIG. 1 shows the present known method. Operator B's hands 16 and 18 can be seen holding a clamp 10 and the free end of the ligature 11. The tip of the ligature is within the jaws of Operator B's clamp 12. Operator's B's clamp 10 extends beneath Operator A's clamp 14 for a distance X. Operator A's clamp 14 is positioned beneath the vessel 13 awaiting passage of the ligature. One ligature has been completed 20 and when the second ligature is completed the vessel will be divided along the dotted line 22.

FIG. 2, in accordance with the present inventions shows four views of a surgical ligature including a predetermined end portion or tip, said end portion has a firm structure with end portion being arranged in cooperative alignment with a sleeve member for passage of end portion therethrough. View (a) shows the firm end portion 24 projecting a distance Y from the sleeve 26. The ligature 28 passes through the channel in the sleeve and trails out the back of the sleeve. Views (b) and (c) depict front and side views of the device. In (d) the tip 24 is shown dislodged from the sleeve 26 and the channel in the sleeve is depicted by dotted lines 30. The ligature 28 is seen passing through the channel.

Figure 3:
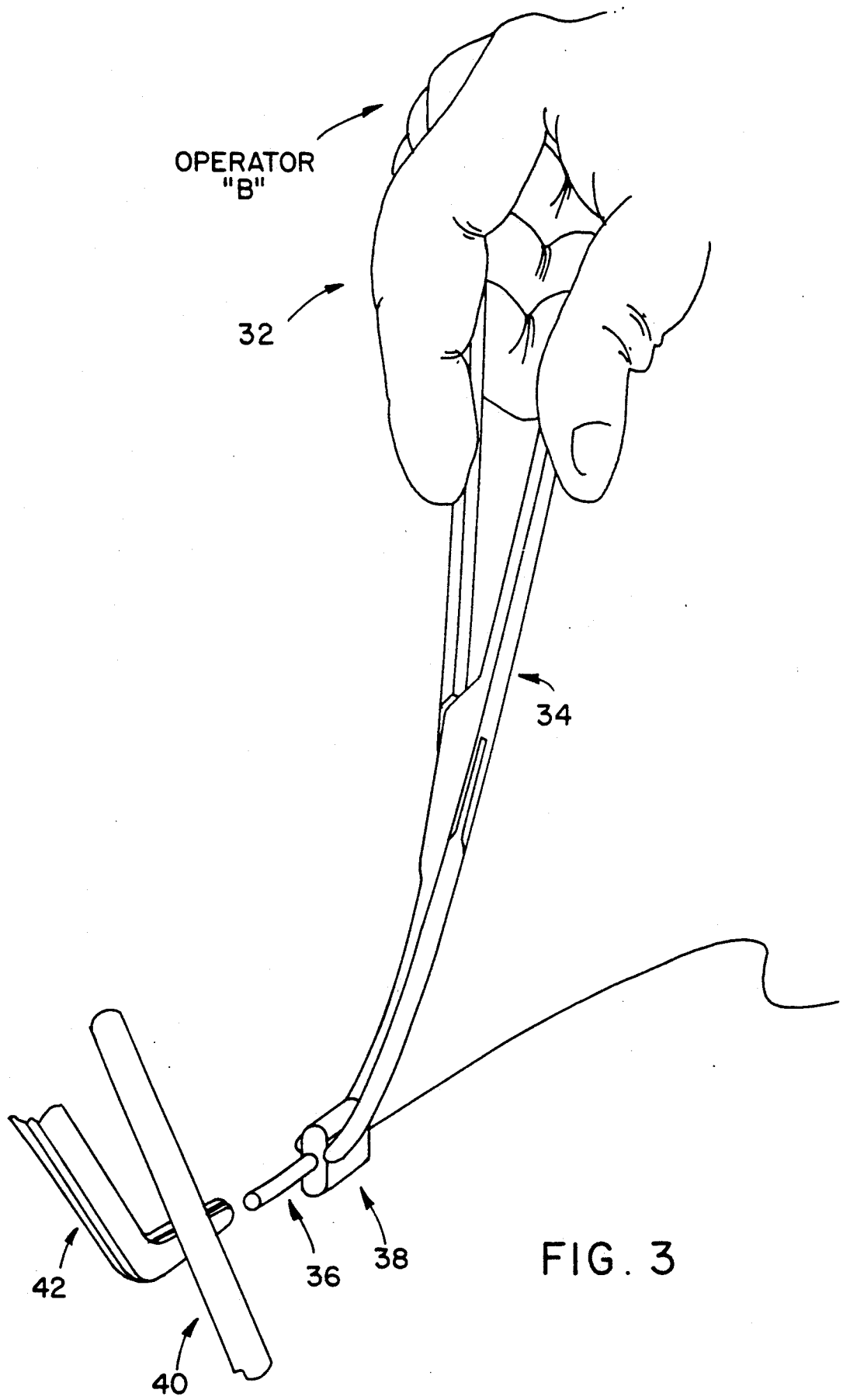
FIG. 3 shows an oblique view of a ligature being passed using the device.

FIG. 3 shows Operator B's hand 1 32 holding a clamp 34 which is presenting the end portion and sleeve 36, 38 to Operator A's clamp 42 which has been positioned under the vessel 40.

Figure 4:
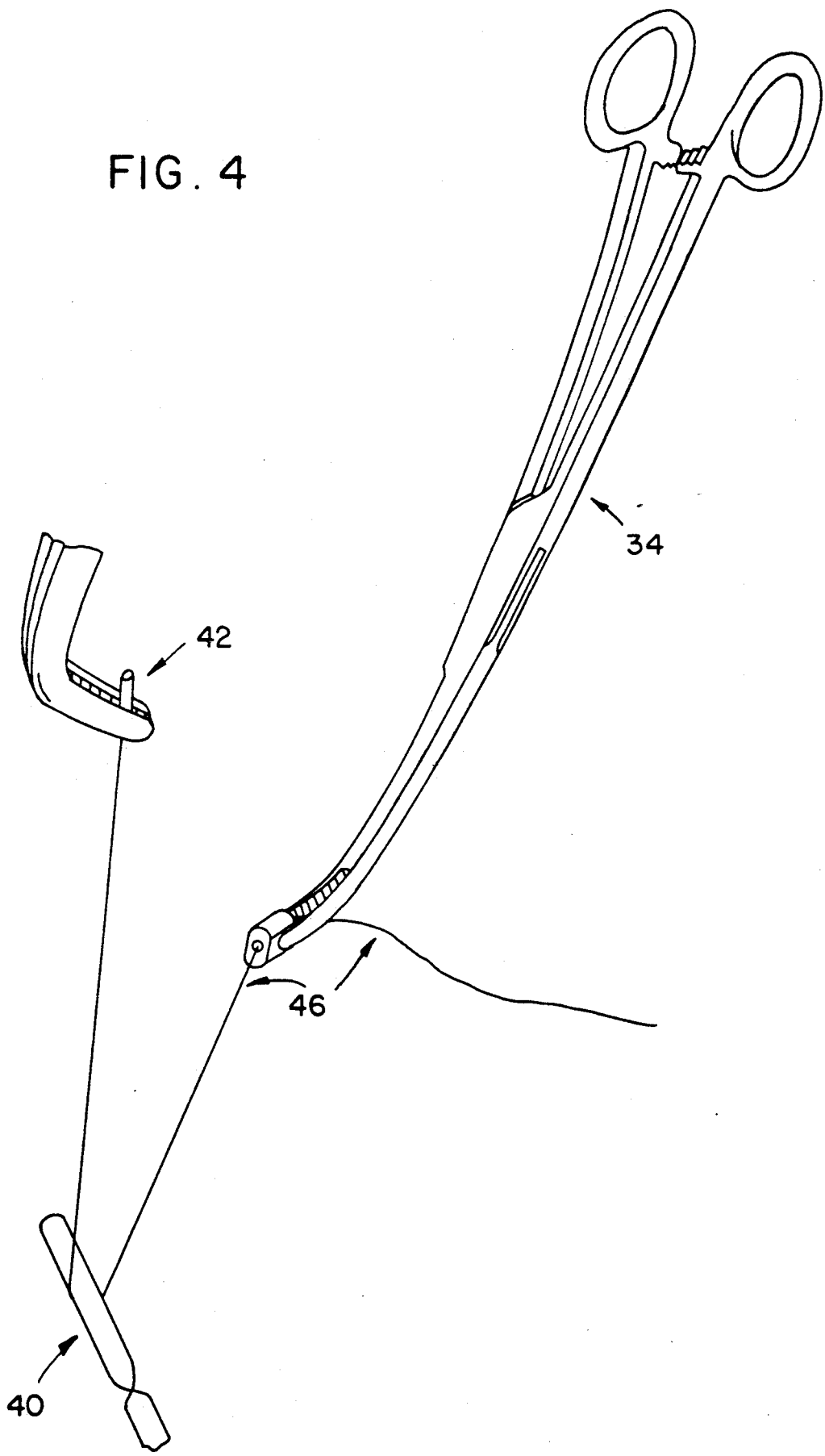
FIG. 4 shows an oblique view of the free end of the ligature being presented up out of the wound.

FIG. 4 shows the completed passage of the ligature tip 42 under the vessel 40 and the free end 46 being lifted out of the wound so that Operator A has easy access to it and may quickly complete the ligation.

Figure 5:
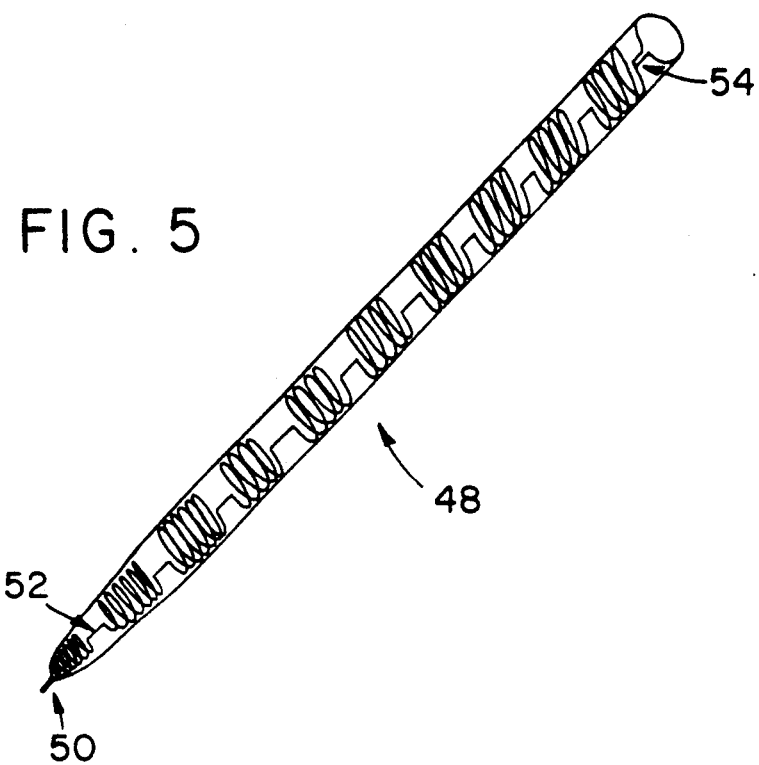
FIG. 5 shows a transparent view of the tubular container with multiple ligatures within.

FIG. 5 shows a system for assembling and arranging surgical ligatures in which multiple ligatures are contained within a hollow tube 48 with the predetermined end portion of the first ligature 50 protruding a predetermined distance so that it can be easily grasped, and upon withdrawal of the first ligature the end portion of the second ligature 52 is located into position.

Figure 6:
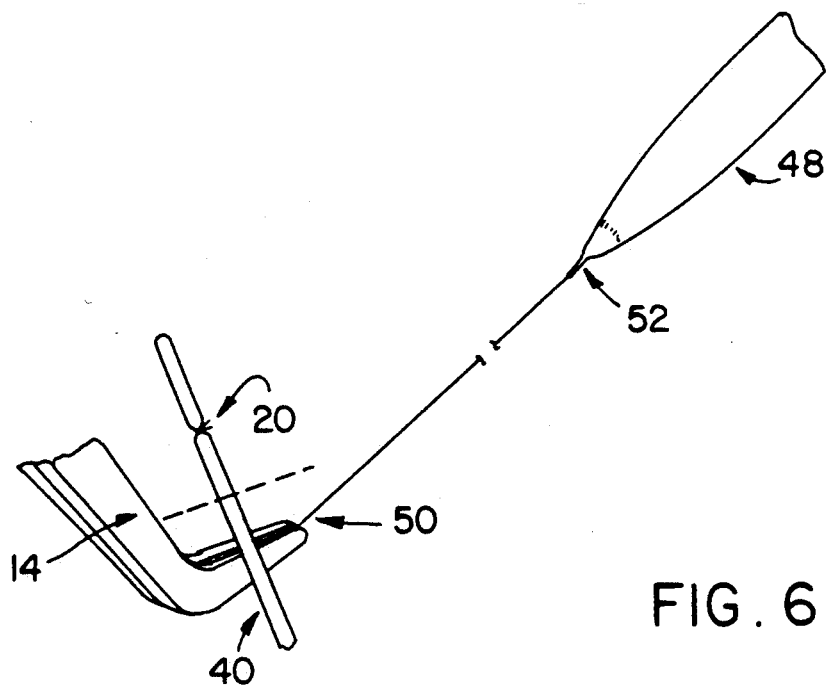
FIG. 6 shows this tubular container in the act of passing a ligature.

FIG. 6 shows a system for assembling and arranging ligatures in which multiple ligatures are contained within a hollow tube 48 with the predetermined end portion of the first ligature 50 having a firm structure protruding a predetermined distance so that it can be easily grasped and upon withdrawal of the first ligature the second ligature is located into position with the "free end" of the first ligature loosely attached to the end portion of the second ligature 52 providing tension whereby to eliminate the need for a sleeve. Furthermore the firm end portions of the ligatures within the containers are color-coded whereby to signify when the dispenser is nearly empty. For example, the firm end portions are initially green, the second and third to the last end portions are yellow and the last firm end portion is red.

What is claimed is:

1. A device for surgical ligation comprising:
a surgical ligature including a first free end, and a second end having a predetermined firm tip means, formed with additional material, for facilitating accurate one-handed passage of the ligature under a tubular vessel wherein said tip means is constructed of a sterilizable surgical grade material whereby injury to the tubular vessel is avoided; a sleeve member in cooperative alignment with said tip means; said sleeve member providing a passage means housing said tip means and providing ready access to said free end of said ligature for efficient ligation of the vessel.

* * * * *